US005562606A

United States Patent [19]
Huybregts

[11] Patent Number: 5,562,606
[45] Date of Patent: Oct. 8, 1996

[54] BI-CAVAL CANNULA

[76] Inventor: Marinus A. J. M. Huybregts, Tobias Asserlaan 129 NL-1111 MG, Diemen, Netherlands

[21] Appl. No.: 362,584
[22] PCT Filed: Jul. 8, 1993
[86] PCT No.: PCT/NL93/00145
§ 371 Date: Jan. 9, 1995
§ 102(e) Date: Jan. 9, 1995
[87] PCT Pub. No.: WO94/01159
PCT Pub. Date: Jan. 20, 1994

[30] Foreign Application Priority Data

Jul. 8, 1992 [NL] Netherlands ............................ 9201222

[51] Int. Cl.$^6$ .................................................. A61M 5/00
[52] U.S. Cl. .................................. 604/8; 604/113; 604/96
[58] Field of Search .................................. 604/96, 178, 7, 604/8, 19, 104, 113, 264, 101, 280, 4

[56] References Cited

U.S. PATENT DOCUMENTS 3,995,617  12/1976  Watkins et al. .......................... 604/4 X
4,309,994   1/1982  Grunwald .

FOREIGN PATENT DOCUMENTS 0161045  11/1985  European Pat. Off. .

OTHER PUBLICATIONS

Leeds, S., "A Cannula for Simultaneous Drainage of Both Cavae in Artificial Heart Experiments", *Proceedings of the Society for Experimental Biology and Medicine*, Oct.–Dec. 1950 (inclusive), vol. 75, pp. 468–469.

*Primary Examiner*—Corrine M. McDermott
*Assistant Examiner*—N. Kent Gring
*Attorney, Agent, or Firm*—Young & Thompson

[57] ABSTRACT

Cannula (1) for direct drainage of venous blood from both venae cavae, comprising an insertion piece (3) for insertion into the venae cavae through the right atrium and a connecting piece (2) secured to the insertion piece (3) for connecting with a suction device. The insertion piece comprises two openings (5, 8) at opposite ends of the insertion piece for draining the superior vena cava and the inferior vena cava respectively. The insertion piece is substantially longer than the distance between the entrances of both venae cavae in the right atrium, and has a diameter allowing insertion through the entrance of one vena cava in the right atrium and to the opposite vena cava. The insertion piece has an opening (8) near a free end, and a side opening (5) near a junction of the insertion piece with the connection piece. The cannula, at least the part that is to be positioned in the juncture of the venae cavae with the right atrium and in the right atrium itself, is provided with cooling structure (9, 12, 15, 23) arranged around the cannula.

20 Claims, 4 Drawing Sheets

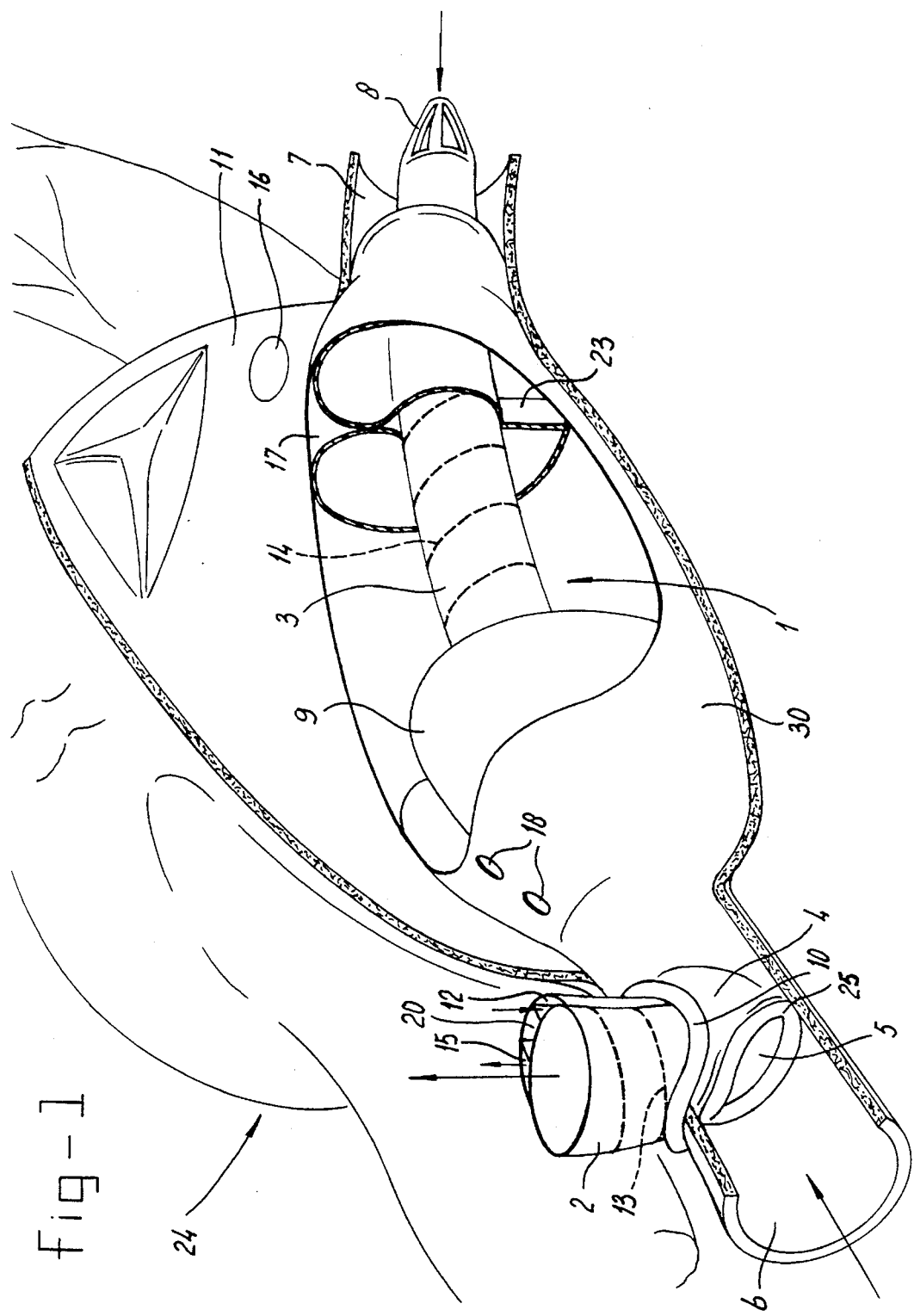

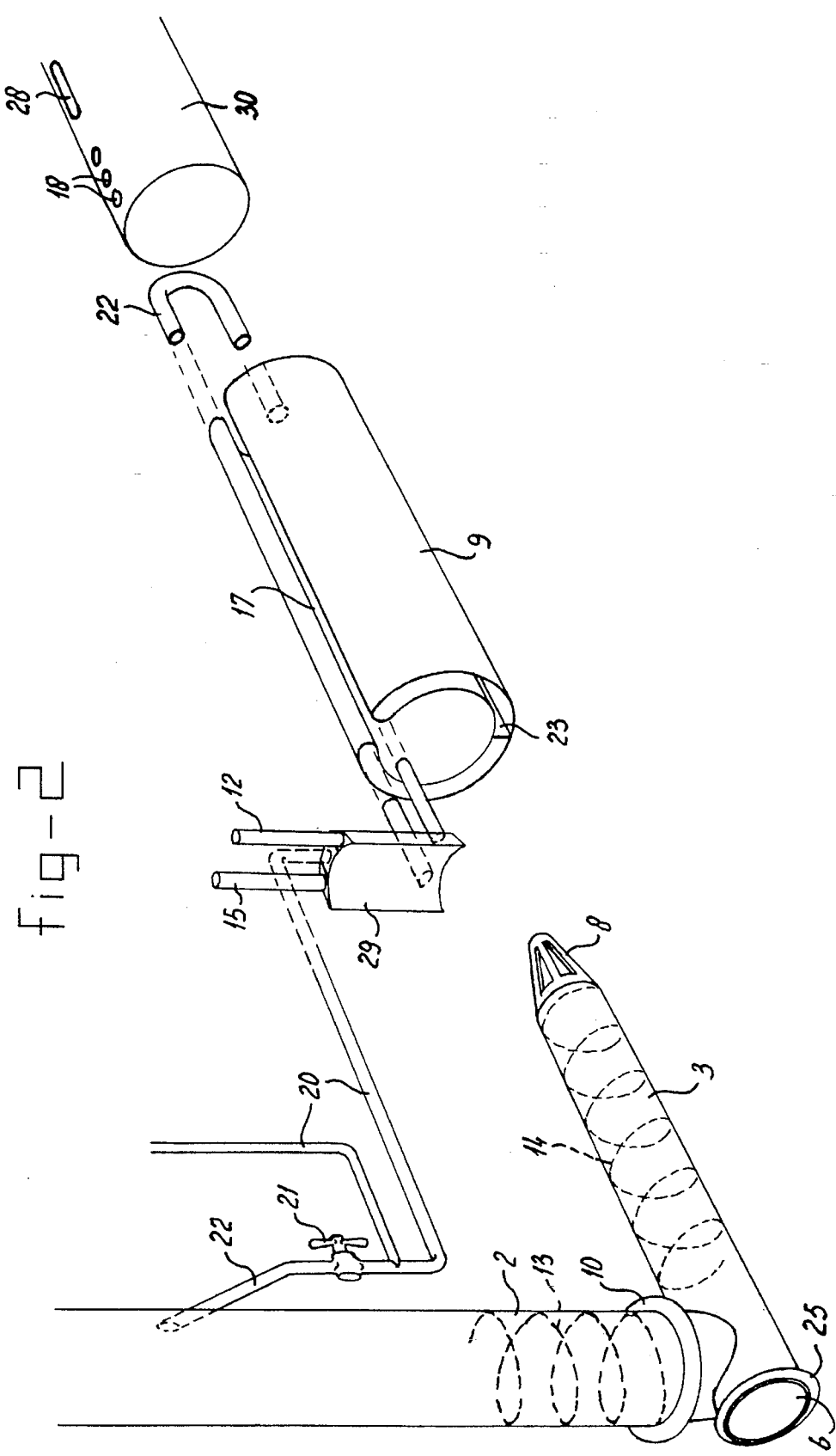

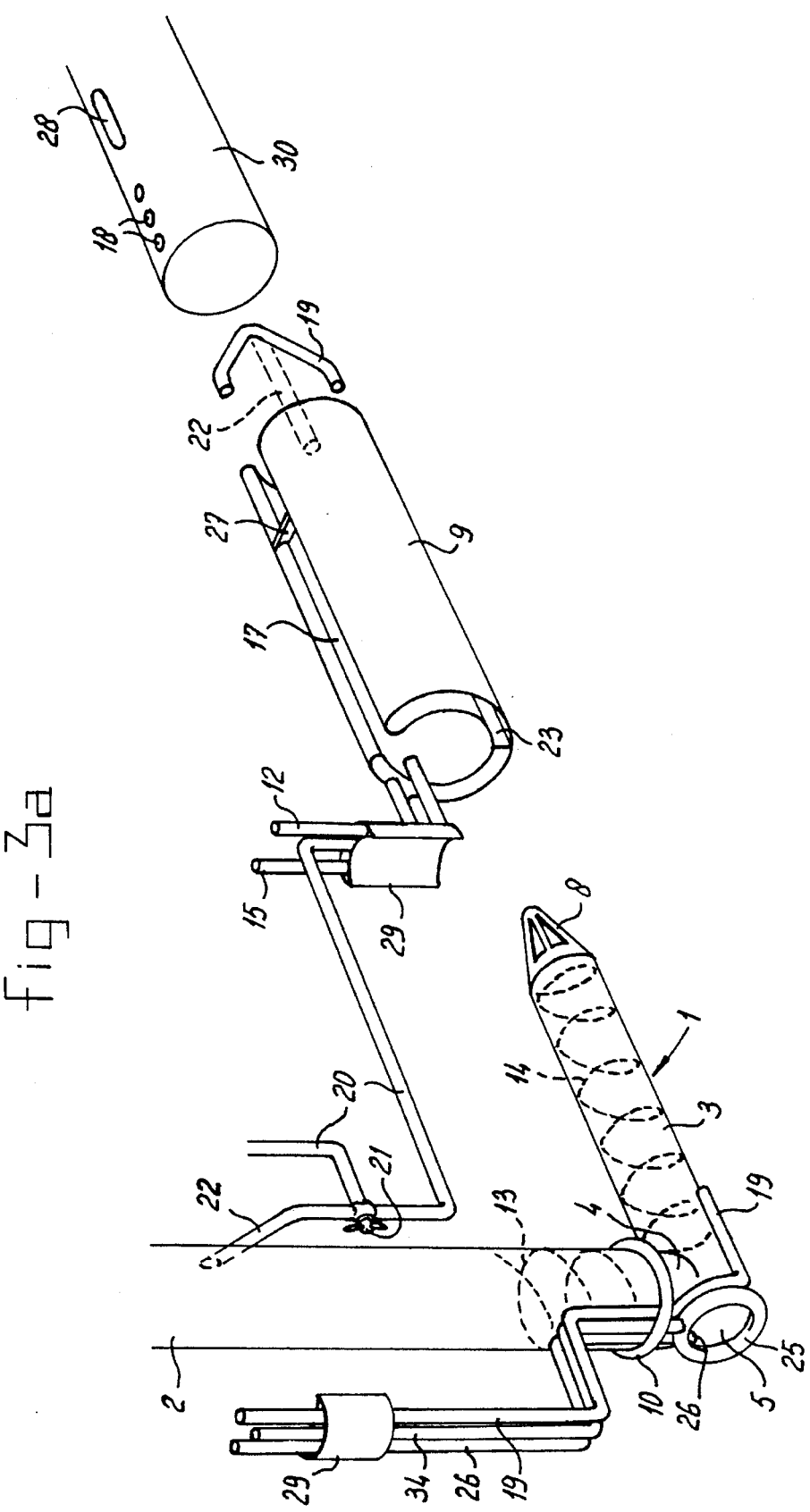

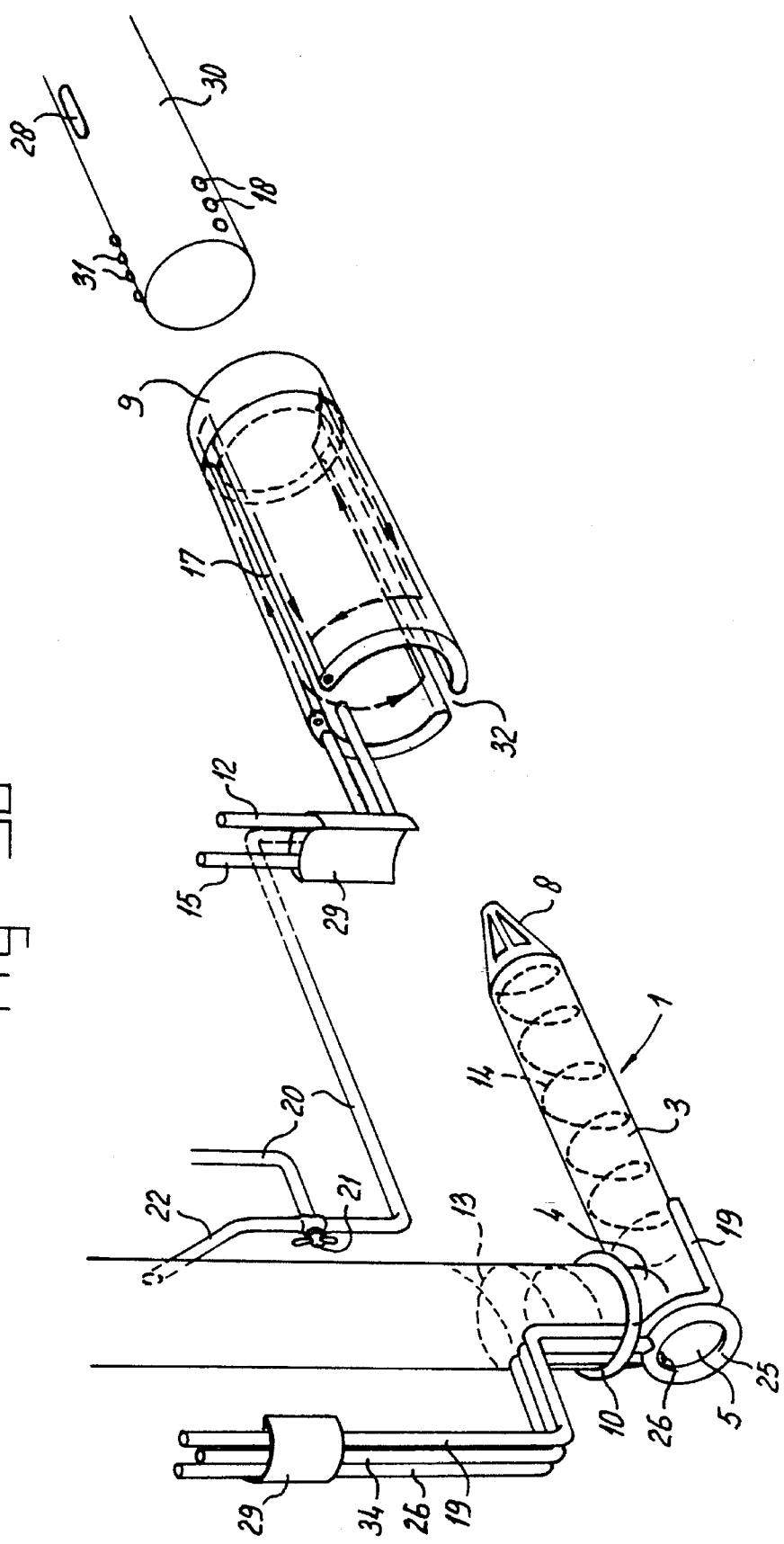

5,562,606

BI-CAVAL CANNULA

FIELD OF THE INVENTION

The invention relates to a cannula for draining venous blood directly from both venae cavae, comprising an insertion piece for insertion into the renee cavae through the right atrium, and a connecting piece for coupling with a suction device, wherein the insertion piece has two openings for draining the superior vena cava and the inferior yens cava respectively.

BACKGROUND OF THE INVENTION

Such a cannula is known from the U.S. patent specification 4,309,994. This patent suggests that an opening in the right atrium is made, through which a cannula with Y-shaped branches can be inserted. One branch goes into the inferior vena cava, while the other goes into the superior vena cava. In this way, blood from both venae cavae can be extract d using one cannula.

Using such a cannula, it is possible to block off or to allow access to either one of the venae cavae, along the cannula to the right atrium, so that, if desired, the right atrium can be shut off from the circulatory system of the body; this is known as total bypass and partial bypass.

Opening the right atrium results in the formation of scar tissue, which can cause heart rhythm disturbances that negatively influence the circulation.

SUMMARY OF THE INVENTION

The subject invention aims to avoid damage to the heart and to make a physiological total bypass technique possible.

This subject is realized with the cannula described above in that the insertion piece is substantially greater in length than the distance between both entrances of the venae cavae in the right atrium, and has a diameter allowing insertion into the right atrium through the entrances of the venae cavae and across into the opposite vena cava, wherein the insertion piece comprises an opening near the free end, and a side opening, near the junction with the connection piece, and in that the cannula is provided sealing means which seal the cannula after insertion through the incision made in the vena cava.

The invention is based on the idea that an incision should no longer be made in the right atrium, but instead, in one of the venae cavae, and that the entrance of the vena cava in the right atrium should be used for introducing the insertion piece of the cannula. To achieve this, either one of the venae cavae must be opened. In both cases, it is also possible to use the cannula for draining blood from the vena cava which received the incision. To this end, it is preferable to make a bend in the cannula, and to make an opening in an extension of the insertion piece. The angle of the bend should, especially, lie in between 90° and 145°. The cannula can drain the blood out of the vena cava which was incised through the side opening, and can drain the blood from the opposite vena cava through the open end of the insertion piece. Both bloodstreams should be drained, via the cannula, into the connecting piece, possibly being lead via an internal profile, designed to promote optimal flow; additionally, the internal diameter of the connecting piece should, in comparison with the internal diameter of the insertion piece, be proportional to the transported bloodstreams.

The proximity of the side opening in the cannula to the insertion point in the vena cars makes means for sealing off the cannula at the insertion point necessary. A flexible flange on the connecting piece, which contacts with the outside of the insertion point, provides such a seal, and can also serve to secure placement of the cannula.

A supplementary seal for the cannula at the insertion point could be a ring-shaped, inflatable seal, or cuff, around the side opening, which can seal off the direct access from the incised yena cava to the right atrium, and also centers the cannula in the yena cava. By using such a seal, partial bypass can be done, because the blood from the side opening and from the insertion part of the cannula can reach the opposite vena cava and from there, the right atrium. For this purpose, an independently inflatable cuff, with a duct containing a valve, can be made.

With partial bypass, and depending on the prevailing pressures, liquid will pass through the cannula via one or both venae cavae to the right atrium, or vice versa, whichever is desired at the moment that the filling of the right atrium and heart on the one side, and the filling of the venae cavae and with that the circulatory system on the other, have to be synchronized. If the circulation is taken over by a heart-lung machine, and heart functions are disconnected, draining the heart and the right atrium will nevertheless be frequently desirable, and this is only possible in a partial bypass situation by draining the whole venous system to an unphysiologically low level.

An exception to this is an open connection, possibly with a one-way valve, between the right atrium and one or both of the venae cavae or the cannula, wherein the ends of the connection are so situated that a venturi effect is generated by the bloodstream, causing the right atrium to be evacuated, despite a higher pressure in the venae cavae. Means that make total bypass possible, and give access to the right atrium and coronary sinus independent of a venturi effect, offer the optimal means of solving the heart conservation problem.

An accepted and frequently used method for conserving the heart during heart operations which are performed on a heart at rest, is to use a heart-lung machine to handle the circulatory system, and to seal off the heart's own coronary system from the circulation, and to flush this with a cold chemical solution—cardioplegia. This stops the contractions of the heart, and the cardiac tissue, temporarily deprived of blood, is conserved, partly due to cooling. This is because cardiac muscle that does not contract, and is cooled, has a lower oxygen requirement.

The problem with this is that the coronary circulation and the heart chambers cannot be fully protected from the circulatory system of the body, and that the heart surface does have contact with warmer direct surroundings, i.e. the body of the patient; the thermal insulation of the heart is thus imperfect. In the right atrium, even though entry of venous blood is hindered by the total bypass, conditions as far as thermal insulation is concerned are even less favorable, partly due to the thermal radiation from the venous cannula or cannulas which are running through it. Because of this, the temperature of the right atrium will hardly deviate from the body temperature of the patient, while it is exactly the right atrium, with sinoatrial node and atrio-ventricular node, that needs to be well conserved by cooling.

The currently used, but only marginally effective solution for this problem is to cool the circulatory blood and therefore the patient so that, because of the smaller heat difference, warming of the heart takes longer. Lowering the body temperature in order to reach an ideal as far as heart-cooling is concerned has, depending on the temperature, disadvantageous consequences for the distribution of blood over various organs and for the distribution of body fluids in various body compartments. Body cooling is therefore a less suitable solution for the problem should no total body circulation-stop be planned.

The invention provides a solution for the thermal insulation and cooling problems for the right atrium, and therefore also for the heart, by providing cooling means, at least around that part of the cannula which has to be inserted into the right atrium and the transitions of the venae cavae in the right atrium, preferably arranged around the insertion piece. To ensure that heat transfer between the right atrium and the cooling system is as effective as possible, the cooling means, according to the preferred embodiment of this invention, comprise an inflatable balloon, which has a separate inlet and outlet duct to allow a continual flow. This inflatable balloon can also function as the seal used for total bypass, by sealing off both venae cavae from the right atrium. It is also possible to integrate the ring-shaped cuff mentioned earlier and this balloon; the separate duct with a valve for filling the cuff would then not be necessary.

Through continuous circulation, and achieving a balance between inflow and outflow of coolant, the balloon can be kept inflated, and ideally should lie as much as possible against the inside wall of the right atrium, so that this is cooled. The heat radiation from the cannula in the right atrium is also diminished by the presence of this same balloon.

To achieve even distribution of coolant through the cooling means, various techniques are possible. It is possible, for example, to position partition walls either lengthwise or spirally in the balloon. It is also possible to position the inlet ducts and outlet ducts concentrically around each other. In the construction of the balloon, allowance must be made for the possible presence of a tourniquet around the superior vena cava or the inferior vena cava: this must not in any way be allowed to block the flow of the coolant. An elasticity gradient in the balloon ensures that it will first collapse at the free end of the insertion piece of the cannula, guaranteeing complete deflation of the balloon.

According to a special embodiment, the balloon is realized such that, when inflated, a gutter is present near to the periphery of the balloon. This gutter can be provided with a cover with one or more outward openings to prevent it from being pressed flat, wherein it is important that at least one of the openings is opposite the mouth of the coronary sinus in the right atrium. During total bypass, liquid which comes from the coronary sinus can be selectively or indirectly drained off via the right atrium, through drainage means, or liquid can be supplied via supply means. Selective access to the coronary sinus and the right atrium can be obtained by making adaptations to a single gutter, or by using more than one gutter.

The drainage means can be, as mentioned before, a connection with an extraction effect, working on the venturi principle, or an outlet duct to a suction device, the output of which can be recirculated to the system, or disposed of, as desired. Supply of liquid via the gutter during total bypass can be indirect via the right atrium, or direct to the coronary sinus, with retrograde cardioplegia as the objective, or supply of liquid to the right atrium, where setting up an artificial lung circulation is the objective.

Selective access to the coronary sinus, with one single gutter and one single access duct, can be achieved by providing one opening in the gutter which, because of its location and shape at that point, comes to lie in or on the mouth of the coronary sinus in the right atrium when the cooling balloon is inflated, thus sealing it off, and, if the balloon is slightly inflated, and/or the cannula is rotated around the length of the insertion piece, lies freely in the right atrium, while maintaining total bypass. If a gutter with more than one opening is used, insertion of a special cannula, through the gutter to the coronary sinus, is possible.

Selective and simultaneous access to the coronary sinus and the right atrium can be achieved by dividing the gutter into two parts—either with a permanent division, or by a one-way valve mechanism, possibly controllable, and operable by reversing the direction of coolant flow in the cooling balloon or by other means where provisions are made for an access duct to both the first and to the second part of the gutter. Here, one part of the gutter has openings which give access to the right atrium, and the other part of the gutter has a single opening, with the features described in the previous paragraph, which provides access to the coronary sinus. Instead of dividing the gutter into two parts, the above can, of course, also be achieved by using more than one gutter. Finally, sealing of the openings in these gutters is possible by using the above-mentioned mechanism for reversing the direction of coolant flow or by a one-way valve mechanism.

A point of measurement with measuring duct for measuring venous pressure can be situated close to the side opening of the cannula.

A tapering basket at the free end of the insertion piece ensures simple insertion of the cannula via the insertion point in the vena cava in question, and ensures unobstructed flow in the cannula. An access duct can be part of the basket.

The invention described above relates to placement via an incision in the superior vena cava or the inferior vena cava, where the cannula then extends into the inferior vena cava or the superior vena cava respectively. Both possibilities can be realized in practice, and the invention is explained further below, using the drawings of various embodiments, wherein an incision in the superior vena cava is assumed.

BRIEF DESCRIPTION OF THE DRAWINGS

The figures show:

FIG. 1—a cut-away view of the cannula, according to the invention, inserted via an opening in the superior vena cava.

FIG. 2—an exploded view of the cannula as depicted in FIG. 1.

FIG. 3a—a first modified embodiment of the cannula depicted in FIG. 2.

FIG. 3b—a variant of the embodiment shown in FIG. 3a.

DETAILED DESCRIPTION OF THE PREFERRED EMBODIMENTS

In FIG. 1, the part of the heart depicted is indicated by number 24. Of special importance are the right atrium 11, the superior vena cava 6 and the inferior yens cava 7. During an operation where the heart function is (temporarily) disconnected, and the circulation is taken over by a heart-lung machine, blood is extracted at the point where the superior and inferior venae cavae join.

According to the invention, a cannula 1 is used for this purpose. This cannula consists of a relative thick connecting piece 2 and a thinner insertion piece 3. Connecting piece 2 and insertion piece 3 are joined to each other by an almost right-angle bend 4. Opening 5, which provides a connection with the superior vena cava is positioned in this bend 4. The free end of the insertion piece 3 is provided with a tapered basket 8. Consequently, the insertion piece can be easily inserted into the superior vena cava 6, be lead through the right atrium 11, and be centered in the inferior vena cava 7. Because of the basket-shaped construction, unobstructed inflow of blood to the cannula from the inferior vena cava is guaranteed. According to the invention, metal spirals 13 and 14 are positioned to prevent buckling of the material from which the connecting piece 2 and the insertion piece 3 are made. The connecting piece can be connected to a state of the art suction device, not depicted.

Because it concerns the extraction part for blood, suction of air by the flow of blood in the cannula is not fatal, but not desirable. With the aid of, for example, a soft flange 10, which, because of flexibility either assumes a sealing position on, or automatically sucks onto the insertion point in the superior vena cava, intake of air can be prevented and the cannula 1 can also be held in place.

An supplementary sealing for the insertion point in the superior vena cars is seal 25, an inflatable, ring-shaped cuff, present on the side opening of the cannula, which can seal off the direct access to the superior vena cava 6 along the cannula to the right atrium 11, and therefore also function as a seal for the cannula with respect to the insertion point in the superior vena cava. The lumen of the seal 25 is connected to the lumen of the cooling balloon 9, to be later described, and can form part of this cooling balloon 9, as is depicted in FIGS. 1 and 2. In addition, seal 25 centers the insertion piece 3 in the superior vane cava.

According to the invention, the cannule 1 is provided with cooling means. These consist of an inlet for coolant 12 and an outlet for coolant 15, positioned near the insertion piece 3 within the periphery of the flange 10 against the cannula, and connected to a cooling mantle, in the form of an inflatable balloon (9).

As is shown in FIG. 1, the balloon 9 is, as it were, wrapped around the insertion piece so that it is possible to insert it, together with the insertion piece, into the right atrium, in a simple way, sad to remove it again in the empty state. By applying pressure in the balloon (coolant pressure), the balloon is inflated, and lies against the walls of the right atrium, as a result of which optimum heat transfer between the coolant and the right atrium is achieved. This is further aided by positioning a partition 23 in the balloon, that itself extends to just before the end of the cooling chamber near to the basket, where it is bordered by the balloon 9, as a result of which even distribution of coolant throughout the cooling chamber is achieved.

Balloon 9 provides furthermore a seal between the right atrium and the superior yens cava and the inferior vene cava. It is also possible to establish a lower pressure, as a result of which, because of an elasticity gradient in the cuff 30, the seal between the right atrium and the inferior vena cava is first broken, followed by a breaking of the seal between the right atrium and the superior vane cava at an even lower pressure, or lack of pressure.

With total bypass, and thus with an inflated balloon 9, access to the right atrium sad the mouth of the coronary sinus in the right atrium is achieved by gutter 17. The gutter is covered with an elastic cuff 30. Opening 28 in the elastic cuff 30 is so positioned and is of such a shape that, with the cooling balloon 9 fully inflated, it contacts with the mouth of the coronary sinus 16 in the right atrium 11, and the openings 18 in the cuff 30 lie unblocked in the right atrium. Blockage of the openings 18, caused by the right atrium wall can, if necessary, be prevented by surface structures 31 on the exterior of cuff 30.

The most plain and simple simultaneous and non-selective access to the right atrium and coronary sinus is achieved by the combination of gutter 17 and access duct 20 with openings 18 and 28 in cuff 30, as depicted in FIG. 1 and FIG. 2.

Possibilities for a venturi generating connection are indicated with 22. Several selection valves, such as 21, can be built into various access ducts. A measuring point for blood pressure with a measuring duct is indicated in its entirety by 26.

In FIGS. 3a and 3b, two further variants of the cannula depicted in FIG. 1 and FIG. 2 are shown. Here, seal 25 is provided with a separate external connection 34, so that seal 25 can be inflated and deflated independently of the balloon (not depicted further). In the embodiment in FIG. 3a, the gutter 17 is provided with a partition 27. Because of this, access to opening 28 for the coronary sinus and opening 1 for the right atrium is separated.

Full and simultaneous selective access to the right atrium and the coronary sinus can be achieved with gutter 17, by positioning openings 18 and 28 in cuff 30, and by placing the partition 27 in gutter 17. If access duct 20 is a double duct, with the lower duct having access to the part of the gutter 17 nearest the basket and the surface duct having access to the part of the gutter 17 nearest the bend of the cannula, then simultaneous access to both halves of the gutter is possible (not depicted).

By placing partition 27, it is also possible to get access to the part of the gutter closest to the bend of the cannula with access duct 20, and to get access to the part of the gutter nearest the basket with access duct 19, running round or along the end of the insertion piece. Here, access duct 19 runs on through into balloon partition 23, and partition 27 can be made permeable so as to allow coolant to also flow through both halves of the balloon.

In the embodiment according to FIG. 3b, except gutter 17, a gutter 32, lying opposite to it, is provided. With the use of two gutters, gutter 17 is, connected to the coronary sinus via opening 28 and access duct 20, and gutter 32 is connected to the right atrium via opening 18 and a shortened access duct 19; the balloon partition 23 is no longer needed, as depicted in FIG. 3b.

Connecting pieces 29 are depicted in FIGS. 2 and 3 at a distance from connection piece 2. In practice, these pieces are, however, positioned against the connection piece, as is indicated by their special shape.

Instead of the examples of cooling balloon 9 embodiments and the means of conducting the coolant flow shown here, it is also possible to realize the supply of coolant under high pressure, with a jet nozzle in the inlet ducts, or for somebody competent in state of the art techniques to produce the cooling means, gutters and access ducts in any other obvious way. By reversing the supply and drainage of the coolant, a suitable valve mechanism can be operated.

It must be realized that by controlling the restriction in the coolant supply or drain, the pressure inside the balloon 9 can be controlled. The coolant can be supplied to or drained from the right atrium and/or the coronary sinus through access ducts 19 and 20.

The cannulas described above can be designed to fit the measurements of the heart of the person to be operated on. The following values are given as guidelines for the cannula measurements for an adult patient:

| | |
|---|---|
| Internal diameter of insertion piece | 8–9 mm |
| Internal diameter of connecting piece | 10–12 mm |
| Length of insertion piece | 10 cm |
| Length of connection piece | 2    25 cm |
| Length of cannulation point | 2 cm |
| Diameter of side opening | 8 mm |

From the above it is clear that with the cannula according to this invention, the following advantages are obtained. The cannula can be placed in one of the venae cavae without any damage to the right atrium. Contact of the venous bloodstream with the heart (and thus warming up) can be prevented by leading the blood through the intracardial part of the cannula, where the inflatable balloon absorbs the heat radiation. This inflatable balloon also takes care of sealing off the superior vena cava and the inferior vena cava from the right atrium, so that surrounding these structures with tourniquets to achieve total bypass becomes unnecessary. It remains however possible to position these tourniquets or slings with a functioning cannula. The total bypass can be achieved after insertion by gradual filling of the balloon, and can be abolished before removal by gradual emptying of the balloon. The presence of the cooling balloon provides cooling for various parts of the right atrium. By avoiding contact with blood, there is less influence of the venous bloodstream of the body on the warming up of the heart, so that the body can be kept at a normothermal value and/or the body does not need to be cooled so much, and can more rapidly be returned to a normothermal value. Luxation of the heart has no influence on the venous bloodstream through the cannula and the flow of liquid through the access ducts and the cooling balloon. The access to the right atrium and the coronary sinus for drainage and administration of liquids is fully controlled. Finally, traction on the sinoatrial node is prevented by the cannula. Because of these advantages, conditions for maximum peroperative conservation of the heart and maintenance of the bodily functions are created. Furthermore, the supraventricular excitor and conduction systems are optimally protected, thus achieving a minimizing of heart rhythm and conduction disturbances.

The following ideas are at the basis of this invention.

Damage to a specialized system, such as the right atrium, should be prevented. This is realized by, among other things, the fact that no traction is applied to the sinoatrial node or to the right atrium.

Should the heart be temporarily stopped and conserved, partly by cooling, then the right atrium should also be conserved through efficient cooling, wherein both the stimulus for contraction from the excitor system and the possibility for cardiac muscle to conduct a stimulus and to contract should be temporarily cut out.

Extreme drainage of the body's venous blood system and body cooling to make a heart operation possible should be replaced by a better method because it causes a shock condition, recovery from which involves the need for large transfusions because of the relatively intensified flow of blood through organ systems and a deregulation of the distribution of body fluids over the body compartments.

Thinning of circulating blood should, in order to maintain blood-plasma concentration and the blood colloid osmotic pressure, be restricted to the minimum; this is achieved by, among other things, total bypass with peroperative maintaining of a physiological filling of the circulatory system of the body, keeping coolant separate from the blood circulation, avoiding cardioplegia after flushing the coronary system, improved organ-specific isolation measures and conservation of the heart, as a result of which the above-mentioned shock condition, where large transfusions are needed, is prevented.

Since the non-coronary flow, primarily flowing through the folds of the pericardium and the walls of the right and left atrium, cannot be stopped, this must be cooled by local measures.

Creation of an artificial lung circulation during total bypass with a controllable temperature and consistency independent of the bodily circulation can improve the conservation of the heart and lungs.

The working load on the left ventricle can be controlled by the degree of occlusion of flow into the right atrium.

Though the invention is described using a preferred embodiment, it must be understood that numerous alterations can be introduced, which, after reading the above, will be obvious to a person skilled in the art. It is, for example, possible to use all sorts of other cooling means, such as tubing wrapped around the cannula, or other structures known in the art around a tube for efficient transfer of heat (cold) to the surroundings, wherein insulation measures ensure that the contents of the tube are not affected. Furthermore, warming can done instead of cooling. The scope of protection is determined by the claims appended.

I claim:

1. Cannula (1) for direct drainage of venous blood from both venae cavae, comprising a tubular insertion piece (3) for insertion into the venae cavae through the right atrium and a tubular connecting piece (2) secured to the insertion piece (3) for connecting with a suction device, wherein the insertion piece comprises two openings (5, 8) at opposite ends of the insertion piece for draining the superior vena cava and the inferior vena cava respectively, wherein the insertion piece is substantially longer than the distance between the entrances of both venae cavae in the right atrium, and has a diameter allowing insertion through the entrance of one vena cava in the right atrium and to the opposite vena cava, wherein the two openings of the insertion piece comprise an opening (8) near a free end remote from said tubular connecting piece (2), and a side opening (5) at an end of the insertion piece (3) opposite said free end, said side opening (5) being disposed near a junction of the insertion piece with the connection piece, said junction being closer to said side opening (5) than to said free end, and wherein the cannula, at least the part that is to be positioned in the juncture of the venae cavae with the right atrium and in the right atrium itself, is provided with cooling means (9, 12, 15, 23) that are arranged around the cannula.

2. Cannula according to claim 1, wherein the cooling means comprise an inflatable balloon (9) with at least one connection for cooling fluid.

3. Cannula according to claim 2, wherein the balloon is arranged so that, in the inflated state, both entrances of the venae cavae in the right atrium are sealed off, wherein due to a gradient in the elasticity, during increased filling of the balloon, first the entrance of the vena cava near the connecting piece to the right atrium is sealed off, and only then the entrance of the other vena cava at the free end of the insertion piece to the right atrium is sealed off.

4. Cannula according to claim 1, wherein the insertion piece of the cannula around the side opening (5) is provided with an inflatable sealing means (25).

5. Cannula according to claim 1, wherein the cooling means comprise an outlet which is relatively large in size, wherein a propelling nozzle is placed in an inlet of said cooking means.

6. Cannula according to claim 1 where the cannula is provided with a flow-enhancing surface structure.

7. Cannula according to claim 1, wherein a measuring point (26) with an access duct for venous blood pressure measurement of the circulation of the body is positioned in the cannula.

8. Cannula according to claim 1, wherein the insertion piece comprises a free end of a tapering basket (8).

9. Cannula according to claim 1, further comprising an elongated member which has a length that is greater than the widest part of the cannula, and which fits into the cannula, wherein said side opening (5) of the cannula is of such a size that it is sealable during placement by said elongated member.

10. Cannula according to claim 1, wherein the cannula is provided with sealing means (10) which seal the cannula after insertion at an insertion point in the vena cava opened by an incision.

11. Cannula according to claim 10, further comprising a balloon, wherein the balloon and the sealing means are connected with each other.

12. Cannula according to claim 11, wherein the balloon defines at least one gutter (17), provided with at least one connection to the exterior of the cannula.

13. Cannula according to claim 12, wherein the connection comprises drainage means with a jet pipe (22) which opens into the insertion piece or the connection piece of the cannula.

14. Cannula according to claim 12, wherein at least one gutter comprises a cover with at least one opening (18, 28), wherein at least one opening (28), lies at the mouth of the coronary sinus in the right atrium when the cannula is in place.

15. Cannula according to claim 12, wherein the gutter (17) comprises separate gutter parts, each provided with a connection.

16. Cannula according to claim 11, wherein the balloon has at least one partition (23).

17. Cannula according to claim 11, wherein the outside of the balloon is provided with a structured surface (31).

18. A method for the direct drainage of venous blood from both venae cavae comprising provision of an opening near the connection of one of the venae cavae to the right atrium in one of said venae cavae, insertion of an insertion piece through said opening, through the right atrium into the opposite vena cava and providing suction through said insertion piece at both said one vena cava and said opposite vena cava wherein cooling is provided at least in the juncture of the venae cavae with the right atrium and in the right atrium itself.

19. A method according to claim 18, wherein first the entrance of the vena cava having the opening is sealed off and only then the entrance of the other vena cava at the other side of the atrium is sealed off.

20. A method according to claim 18, wherein sealing is provided between said insertion piece and said opening.

* * * * *